United States Patent
Crawford

(10) Patent No.: US 8,989,902 B1
(45) Date of Patent: Mar. 24, 2015

(54) USER INTERFACE FOR A TELE-OPERATED ROBOTIC HAND SYSTEM

(71) Applicant: Anthony L. Crawford, Rigby, ID (US)

(72) Inventor: Anthony L. Crawford, Rigby, ID (US)

(73) Assignee: U.S. Department of Energy, Washington, DC (US)

( * ) Notice: Subject to any disclaimer, the term of this patent is extended or adjusted under 35 U.S.C. 154(b) by 165 days.

(21) Appl. No.: 13/868,185

(22) Filed: Apr. 23, 2013

Related U.S. Application Data

(60) Provisional application No. 61/772,750, filed on Mar. 5, 2013.

(51) Int. Cl.
| | |
|---|---|
| *B25J 13/02* | (2006.01) |
| *B25J 9/16* | (2006.01) |
| *G01B 21/16* | (2006.01) |
| *B25J 13/08* | (2006.01) |
| *A61B 5/00* | (2006.01) |
| *A61B 19/00* | (2006.01) |

(52) U.S. Cl.
CPC ............... *B25J 9/161* (2013.01); *G01B 21/16* (2013.01); *B25J 9/1689* (2013.01); *A61B 5/6826* (2013.01); *B25J 13/02* (2013.01); *A61B 2019/223* (2013.01); *A61B 5/6806* (2013.01); *B25J 13/082* (2013.01); *A61B 2019/2273* (2013.01)
USPC .......................................................... 700/257

(58) Field of Classification Search
CPC ................................. B25J 9/161; G01B 21/16
USPC .......................................................... 700/257
See application file for complete search history.

(56) References Cited

U.S. PATENT DOCUMENTS

| | | | | |
|---|---|---|---|---|
| 5,004,391 | A * | 4/1991 | Burdea | 414/6 |
| 5,858,291 | A * | 1/1999 | Li et al. | 264/105 |
| 7,472,047 | B2 * | 12/2008 | Kramer et al. | 703/6 |
| 8,682,489 | B2 * | 3/2014 | Itkowitz et al. | 700/258 |
| 2002/0198472 | A1 * | 12/2002 | Kramer | 600/595 |
| 2006/0115348 | A1 * | 6/2006 | Kramer | 414/5 |

(Continued)

OTHER PUBLICATIONS

Kobayashi et al., "Multiple Joints Reference for Robot Finger Control in Robot Hand Teleoperation," 2012 IEEE/SICE International Symposium on System Integration (SII), Kyushu University, Fukuoka, Japan, Dec. 16-18, 2012.

(Continued)

*Primary Examiner* — Jason Holloway
(74) *Attorney, Agent, or Firm* — James B. Potts; Brian J. Lally; John T. Lucas

(57) ABSTRACT

Disclosed here is a user interface for a robotic hand. The user interface anchors a user's palm in a relatively stationary position and determines various angles of interest necessary for a user's finger to achieve a specific fingertip location. The user interface additionally conducts a calibration procedure to determine the user's applicable physiological dimensions. The user interface uses the applicable physiological dimensions and the specific fingertip location, and treats the user's finger as a two link three degree-of-freedom serial linkage in order to determine the angles of interest. The user interface communicates the angles of interest to a gripping-type end effector which closely mimics the range of motion and proportions of a human hand. The user interface requires minimal contact with the operator and provides distinct advantages in terms of available dexterity, work space flexibility, and adaptability to different users.

19 Claims, 9 Drawing Sheets

(56) References Cited

U.S. PATENT DOCUMENTS

2007/0016174 A1* 1/2007 Millman et al. .......... 606/1
2011/0118752 A1* 5/2011 Itkowitz et al. .......... 606/130

OTHER PUBLICATIONS

Kobayashi et al., "Two-Fingered Haptic Device for Robot Hand Teleoperation," Journal of Robotics, vol. 2011, Article ID 419465 (2011).

Kofman et al., "Teleoperation of a Robot Manipulator Using a Vision-Based Human-Robot Interface," IEEE Transactions of Industrial Electronics, vol. 52, No. 5, (2005).

Schaffelhofer et al., "A new method of accurate hand- and arm-tracking for small primates," J. Neural Eng. 9 (2012).

Zhuang et al., "Decoding 3-D Reach and Grasp Kinematics From High-Frequency Local Field Potentials in Primate Primary Motor Cortex," IEEE Transactions on Biomedical Engineering, vol. 57, No. 7 (2010).

* cited by examiner

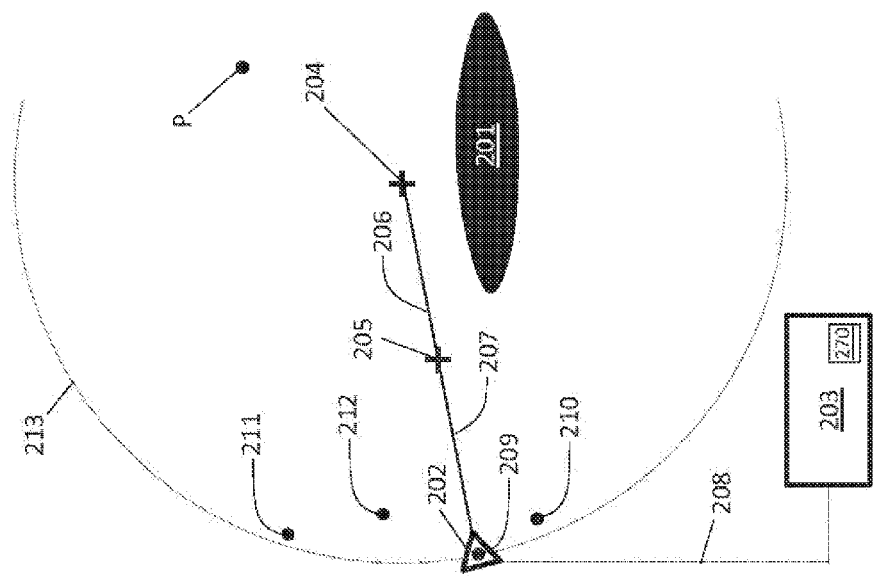
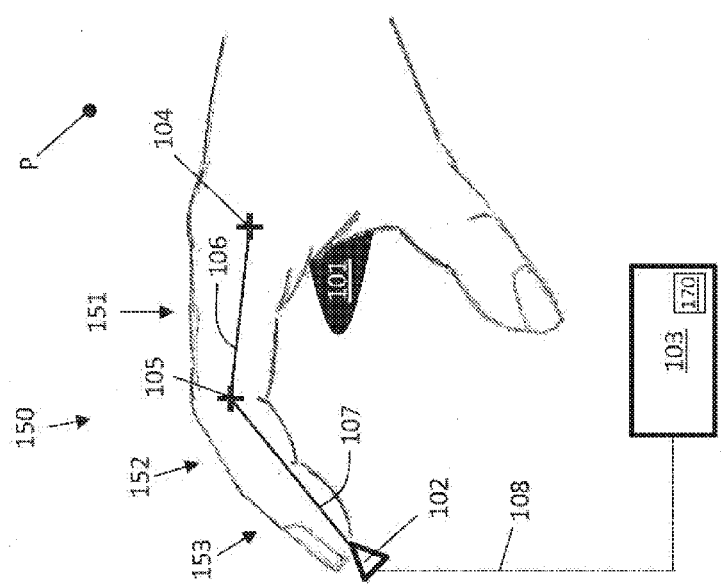
FIG. 1
FIG. 2

| | I | II | III | IV | V |
|---|---|---|---|---|---|
| Average Distal Phalange Length (mm) | 29.4 | 18.1 | 20.1 | 20.0 | 17.3 |
| Average Intermediate Phalange Length (mm) | 0 | 26.7 | 31.7 | 30.8 | 21.8 |
| Average Proximal Phalange Length (mm) | 36.5 | 45.7 | 49.6 | 45.5 | 38.0 |
| Average Metacarpal Length (mm) | 46.8 | | | | |

USER INTERFACE FOR A TELE-OPERATED ROBOTIC HAND SYSTEM

RELATION TO OTHER APPLICATIONS

This patent application claims priority from provisional patent application 61/772,750 filed Mar. 5, 2013, which is hereby incorporated by reference.

GOVERNMENT INTERESTS

The United States Government has rights in this invention pursuant to Contract No. DE-AC07-05ID14517, between the U.S. Department of Energy (DOE) and Battelle Energy Alliance, LLC.

FIELD OF THE INVENTION

One or more embodiments refer to a user interface for the teleoperation of a robotic hand. The user interface conducts a calibration procedure to determine a user's applicable physiological dimensions and applies the physiological dimensions and a specific fingertip location to treat the user's finger as a two link three degree-of-freedom serial linkage, in order to determine angles of interest through reverse kinematics. The user interface communicates the angles of interest to a gripping-type end effector which closely mimics the range of motion and proportions of a human hand.

BACKGROUND

Teleoperation involves operation of a machine at a distance, and is commonly associated with robotics. Early applications were originally intended for manipulation of radioactive, biohazardous, or otherwise inaccessible materials using robotic arms, however in more recent developments they have been used in applications such as robotically-assisted surgery and in space.

A particular variety of teleoperated devices utilize user control of a gripping-type end effector intended to closely approximate the digits of a human hand. Typically these gripping-type end effectors are designed to replicate the hand motion and posture of the controlling operator. Correspondingly, commonly used mechanical human-machine interfaces include a variety of devices worn by the operator, such as exoskeletal mechanical devices, instrumented gloves, motion tracking sensors, or muscular activity sensors. These devices inevitably require direct or close contact with the operator, and as a result may hinder dexterous human motion due to the presence of sensors, attached cables, or other instruments associated with the interface. Other mechanical human-machine interfaces have involved approaches such as dials, joysticks, a computer mouse, or computer graphical interfaces, however these require unnatural operator motions which do not directly translate to the motions of the gripping-type end effector itself. This situation greatly limits the realizable dexterity of the gripping-type end effector, that may be unnatural and must be learned Natural movements are important elements in using teleoperated equipment if complex and speedy manipulation tasks are to be accomplished, particularly if the manipulation is required to take place in hazardous environments such as hot cells, glove boxes, explosives disarmament, space, and others. It would be advantageous to provide a user interface requiring minimal contact with the operator, in order to allow for a wide working space and range of motions. It would be additionally advantageous if such an interface could operate in a manner that adapts to each specific user through calibration, in order to accommodate the wide range of hand physiologies that might be encountered among differing operators. Such an interface would provide distinct advantages in terms of available dexterity, work space flexibility, and adaptability of different users.

Disclosed here is a user interface for a robotic hand intended to monitor and discern the posture of a user's hand during typical grasping and/or manipulation motions, based on tracking the locations of the user's fingertips relative to some fixed reference point. The user interface substantially anchors a user's palm in a relatively stationary position, and relay various angles of interest to a robotic hand having substantially the same configuration and proportions. The user interface acts to anchor the user's palm in a relatively stationary position and orientation, conducts a calibration procedure to determine the user's applicable physiological dimensions, and determines the angles associated with the metacarpophalangeal (MCP) and proximal interphalangeal (PIP) joints of the user's finger necessary to achieve the specific fingertip location. The user interface communicates the respective angles to a gripping-type end effector which will typically closely mimic the user's available range of motion and a typical human proportion.

These and other objects, aspects, and advantages of the present disclosure will become better understood with reference to the accompanying description and claims.

SUMMARY

The user interface monitors the motions and posture of a user's hand during typical grasping and/or manipulation motions and relays various angles of interest to a robotic hand having substantially the same configuration and proportions. The user interface anchors a user's palm in a relatively stationary position and tracks the locations of the user's fingertips relative to some fixed reference point.

The user interface initially conducts a calibration procedure to determine an overall length of a user's finger from the fingertip to the MCP joint, and determine appropriate lengths for the proximate, intermediate, and distal phalange lengths specific to the user. With this information, the user interface determines MCP and PIP angles of the user's finger when a specific fingertip location is reported. A digital controller is configured to receive the specific fingertip location and conduct reverse kinematics to determine the specific angles. The digital controller treats the distal interphalangeal (DIP) joint as passive and treats the user finger as a two link three degree-of-freedom serial linkage having links equal to the lengths determined during the calibration procedure. In an embodiment, the digital controller communicates the respective angles to a robotic hand having proportions commensurate with the average proportions of a human hand.

In an embodiment, the user interface is further comprised of a wrist and elbow assembly mimicking the range of motion available in a human arm. In this embodiment, the digital controller additionally performs a calibration produce to discern the forearm and arm lengths of an individual user, and determines necessary shoulder and elbow joint angles based on reported wrist locations in a process similar to that implemented for the finger size determinations discussed above.

The user interface requires minimal contact with the operator and allows for a wide working space and range of motions. The user interface further adapts to each specific user in order to accommodate the wide range of hand physiologies that might be encountered among differing operators. Correspondingly, the user interface provides distinct advantages in terms of available dexterity, work space flexibility, and adaptability to different users.

The novel process and principles of operation are further discussed in the following description.

BRIEF DESCRIPTION OF THE DRAWINGS

FIG. 1 illustrates an embodiment of the user interface.

FIG. 2 illustrates the calibration procedure of the user interface.

DETAILED DESCRIPTION

Figure 3A:
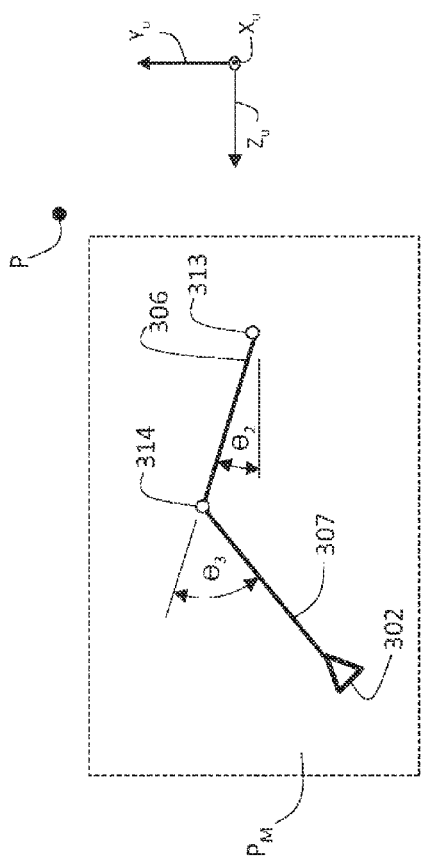
FIG. 3A illustrates a first view of a user planar linkage.

The following description is provided to enable any person skilled in the art to use the invention and sets forth the best mode contemplated by the inventor for carrying out the invention. Various modifications, however, will remain readily apparent to those skilled in the art, since the principles of the present invention are defined herein specifically to provide a user interface for a teleoperated robotic hand system where the user interface acts to infer the MCP and PIP angle of a human operator based on fingertip location.

The user interface is intended to monitor the motions and posture of a user's hand during typical grasping and/or manipulation motions, and relay various angles of interest to a robotic hand having substantially the same configuration and proportions. The user interface acts to anchor the user's palm in a relatively stationary position and orientation, and track the locations of the user's fingertips relative to some fixed reference point. The user interface initially conducts a calibration procedure based on reported fingertip locations in order to determine an overall length of a user's finger from the fingertip to the MCP joint, and determine appropriate lengths for the proximate, intermediate, and distal phalange lengths specific to the user. With this information, the user interface determines MCP and PIP angles of the user's finger necessary to achieve a specific fingertip location reported, and communicates this information to the robotic hand. In this manner, the general motions and posture of a user's hand may be reproduced by the robotic hand. The particular interface has the advantage of adapting to a specific user through the calibration procedure and reporting the user finger angles without direct measurement of the joints of the user's finger, allowing for increased freedom and precision of movement.

Some principles of the user interface are illustrated at FIG. 1. FIG. 1 illustrates a user's hand placed on a palm anchoring section 101, and further illustrates a finger 150, the proximal phalange 151 of finger 150, the intermediate phalange 152 of finger 150, and the distal phalange 153 of finger 150. Additionally illustrated is MCP joint 104 and PIP joint 105 of finger 150, where user proximal phalange length 106 extends from MCP joint 104 and PIP joint 105. At FIG. 1, the hand is maintained in contact with palm anchoring section and is generally stable, so that the location of MCP joint 104 is relatively constant as the finger may be moved during, for example, a finger adduction or abduction. Additionally, as is understood, finger 150 also possesses a DIP joint (not shown) between intermediate phalange 152 and distal phalange 153, which enables additional flexure and compliance.

Additionally illustrated at FIG. 1 is fingertip locator 102, located generally at the fingertip of finger 150. User intermediate-distal phalange length 107 extends from PIP joint 105 to fingertip locator 102. Fingertip locator 102 maintains contact with the fingertip of finger 150, so that motion and relocation of finger 150 generates corresponding motion and relocation of fingertip locator 102. A digital controller 103 is in data communication with fingertip locator 102 through connection 108. Fingertip locator 102 communicates indications of a specific fingertip location to digital controller 103, where the specific fingertip location is relative to a fixed reference point such as reference point P. With fingertip locator 102 maintaining contact with the fingertip of finger 150, the specific fingertip location communicated to digital controller 103 is representative of the fingertip location of finger 150.

Fingertip locator 102 may be any means sufficient to determine a specific fingertip location relative to the fixed reference point. For example, in a specific embodiment, fingertip locator 102 is a specific mechanical linkage connecting finger locator 102 to palm anchoring section 101, as will be discussed. However, other means may be used without violating the spirit of this disclosure. For example, fingertip locator 102 may be a visual marker system, an electromagnetic tracking system, or others systems sufficient to report a fingertip location with respect to a fixed reference point. See e.g. Zhuang et al., "Decoding 3-D Reach and Grasp Kinematics From High-Frequency Local Field Potentials in Primate Primary Motor Cortex," *IEEE Transactions on Biomedical Engineering*, 57(7) (2010); see also Schaffelhofer et al., "A new method of accurate hand- and arm-tracking for small primates," *Journal of Neural Engineering* 9 (2012); see also Kofman et al., "Teleoperation of a Robot Manipulator Using a Vision-Based Human-Robot Interface," *IEEE Transactions on Industrial Electronics* 52(5) (2005), among others.

Digital controller 103 is a digital computer system that can be programmed to conduct the calibration procedure and determine at least a first MCP angle, a second MCP angle, and a PIP angle according to the methods of this disclosure, as will be discussed. Any digital computer system may be employed provided that the digital computer is capable of performing operations as described. Once the digital computer is programmed to perform particular functions pursuant to instructions from program software that implements the operations and methods disclosed, such digital computer systems in effect become special-purpose computers particular to the disclosure. The techniques necessary for programming a digital computer to conduct the calibration procedure and determine at least a first MCP angle, a second MCP angle, and a PIP angle according to the methods of this disclosure are well-known to those skilled in the art of computer systems. Such programming may be stored in a storage medium such as distribution media, intermediate storage media, the execution memory of a computer, or any other medium or device capable of storing for later reading by a digital computer implementing the operations and methods disclosed. When such a program is to be run, they may be loaded from the storage medium into the execution memory of the digital computer, configuring the digital computer to act in accordance with the operations and method disclosed. Such operations are well-known to those skilled in the art of computer systems.

Digital controller 103 is configured to receive the indications of the specific fingertip location and conduct reverse kinematics using at least the specific fingertip location, the location of MCP joint 104, the proximal phalange length 106, and intermediate-distal phalange length 107, as will be discussed. Digital controller 103 treats the DIP joint (not shown) between intermediate phalange 152 and distal phalange 153 as passive, and analyzes finger 150 as a two link three degree of freedom serial linkage, having a first link equal in length to user proximal phalange length 106 between MCP joint 104 and PIP joint 105 and having a second link equal in length to user intermediate-distal phalange length 107 between PIP joint 105 and fingertip locator 102. The DIP joint may be assumed to have any joint angle consistent with the possible motion of finger 150. Typically, the DIP joint is treated as assuming an orientation that achieves less than about a 30° joint angle for distal phalange 153 relative to intermediate phalange 152. Digital controller 103 treats the DIP joint as establishing a constant joint angle for distal phalange 153 relative to intermediate phalange 152 at all specific fingertip locations reported by fingertip locator 102. Digital controller 103 receives the indications of the specific fingertip location and conducts reverse kinematics to discern a first MCP angle, a second MCP angle, and a PIP angle necessary for a given user to achieve the specific fingertip location, based on the results of the calibration procedure conducted. Digital controller 103 outputs the first MCP angle, the second MCP angle, and the PIP angle to a data port 170 comprising digital controller 103. The user interface thereby detects the specific fingertip location and provides information describing the necessary physical action of the user's finger.

The data port 170 comprising digital controller 103 may further communicate the first MCP angle, the second MCP angle, and the PIP angle to a device providing a representation of the user's finger. In an embodiment, the device is a robotic hand controller controlling a robotic finger, where the robotic finger has at least a robotic MCP joint and a robotic PIP joint. The robotic finger may be a physical object where the robotic MCP joint and a robotic PIP joint are joined by physical robotic lengths, or may be a non-physical representation such as an image, provided that the robotic MCP joint and a robotic PIP joint comprise some portion of the image.

In order to conduct reverse kinematics using the specific fingertip location, the location of MCP joint 104, the proximal phalange length 106, and the intermediate-distal phalange length 107, digital controller 103 is programmed to conduct a calibration process in order to determine a user MCP joint location relative to the fixed reference point, a user proximal phalange length, and a user intermediate-distal phalange length. The digital controller is configured to receive a plurality of calibration point locations from fingertip locator 102, and where each calibration point location in the plurality has a unique location relative to fixed reference point P, and where the quantity of calibration points is at least equal to four. Utilizing the plurality of calibration locations, the digital controller determines the center of a calibration sphere. The calibration sphere as described herein is a sphere having a calibration sphere radius and calibration sphere center defining a calibration sphere surface. The calibration sphere is defined such that each calibration point location in the plurality of calibration point locations is displaced from the calibration sphere surface by no more than 10% of the calibration sphere radius. Once the calibration sphere is defined, the digital controller establishes the location of the user MCP joint at the center of the defined calibration sphere. Additionally, the digital controller defines a user finger length by assuming that a user's finger is maintained substantially straight during generation of the plurality of calibration points, and sets the user finger length equal to a value within 95% to 105% of the calibration sphere radius.

The digital controller defines the calibration sphere by treating the plurality of calibration point locations as point cloud data, and determining a best fit sphere using known fitting techniques, such as least-squares fitting, m-estimation, or other techniques. See e.g., Flory et al., "Fitting curves and surfaces to point clouds in the presence of obstacles," *Computer Aided Geometric Design* 26 (2009) and references therein; see also Zhou et al., "Sphere Target Fitting of Point Cloud Data Based on M-estimation," fskd vol. 1, pp. 296-299, 2009 Sixth International Conference on Fuzzy Systems and Knowledge Discovery (2009) and references therein; see also Taubin, "Estimation of Planar Curves, Surfaces, and Nonplanar Space Curves Defined by Implicit Equations with Applications to Edge and Range Image Segmentation," *IEEE Transactions on Pattern Analysis and Machine Intelligence* Vol. 13(11) (1991) and references therein, among others. In an embodiment, the best fit sphere is a sphere having a calibration surface that intersects at least four calibration point locations, as will be discussed. The digital controller may determine the best fit sphere by utilizing commercially available existing software packages capable of determining best fit spheres from point cloud data, such as MATLAB available from The MathWorks Inc., Nattick, Mass., USA, among others. The specific means by which the digital controller determines the best fit sphere is not limiting, provided that the digital controller, establishes the calibration sphere as a best fit sphere where each calibration point location in the plurality of calibration point locations is displaced from the calibration sphere surface by no more than 10% of the calibration sphere radius.

In an embodiment, the digital controller selects four calibration point locations from the plurality of calibration point locations, ensures that at least three of the four points are non-collinear and that all four of the points are not co-planer, and defines the calibration sphere as a sphere having a calibration surface that intersects each of the four calibration point locations. In an embodiment, each of the four calibration point locations is displaced from every other calibration point location of the four by at least inch. As an example, FIG. 2 illustrates a plurality of four calibration point locations 209, 210, 211, and 212 located by digital controller 203 based on indications provided by fingertip locator 202 through connection 208. As illustrated, each of the four calibration point locations describes a unique location relative to fixed reference point P. Digital controller 203 utilizes the four calibration point locations 209, 210, 211, and 212 and defines the calibration sphere, shown partially at 213. The calibration sphere is a sphere having a surface that intersects each of the four calibration point locations in the plurality of calibration points.

Having defined the calibration sphere, digital controller 203 establishes the location of user MCP joint 204 based on the center of the calibration sphere. Digital controller 203 additionally defines a user finger length by assuming that a user's finger is maintained substantially straight during generation of the plurality of calibration points, and establishes the user finger length as equal to 95% to 105% of the radius of the calibration sphere, and preferably equal to the radius of the calibration sphere. Digital controller 203 proceeds to divide the user finger length into a first length and a second length and establishes user proximal phalange length 206 equal to the first length and user intermediate-distal phalange length 207 equal to the second length, such that user proximal phalange length 206 added to user intermediate-distal phalange length 207 is equal to 95% to 105% of the user finger length, and preferably equal to the user finger length.

As used herein, the phrase "defining a center of a calibration sphere" means treating the plurality of calibration point locations as point cloud data, and determining a best fit sphere using known fitting techniques, such as least-squares fitting, m-estimation, or other techniques. Additionally, "calibration sphere radius" means the radius of the calibration sphere. Additionally, the phrase "determining a user finger length based on the calibration sphere radius" means establishing the user finger length as equal to a value within 95% to 105% of the value of the calibration sphere radius. Additionally, the phrase "dividing the user finger length into a first length and a second length based on the user finger length" means establishing a first length and a second length such that the first length plus the second length is greater than or equal to 0.95 times the user finger length and less than or equal to 1.05 times the user finger length.

In an embodiment, the first length and the second length are established based on the average proportions of a human hand and the digit of the hand used for the calibration procedure. In this embodiment, a user length ratio $L_{P\text{-}AVG}/(L_{D\text{-}AVG}+L_{I\text{-}AVG})$ is equal to an average proximal phalange length $L_{P\text{-}AVG}$ divided by the sum of an average distal phalange length $L_{D\text{-}AVG}$ added to an average intermediate phalange length $L_{I\text{-}AVG}$. The average distal phalange length, the average intermediate phalange length, and the average proximal phalange length for the appropriate digit are taken from FIG. 7, which illustrates a user hand with digits designated as I, II, III, IV, and V and associated average lengths in millimeters. In an additional embodiment, when the digit of the hand used for the calibration procedure is a thumb (digit I), the first length and the second length are established based on a thumb user length ratio $L_{M\text{-}AVG}/(L_{P\text{-}AVG}+L_{D\text{-}AVG})$, where $L_{M\text{-}AVG}$ is the digit I average metacarpal length, $L_{P\text{-}AVG}$ is the digit I average proximal phalange length, and $L_{D\text{-}AVG}$ is the digit I average distal phalange length. In these embodiments, the first length divided by the second length is within 10% of the user length ratio for the specific digit, and preferably equal to the user length ratio for the specific digit. Establishing the first length and the second length based on the average proportions of the human hand and the digit used for the calibration procedure allows user proximal phalange length 206 and user intermediate-distal phalange length 207 to closely mimic the anatomy of a finger in contact with and imparting motion to a fingertip locator.

Figure 7:
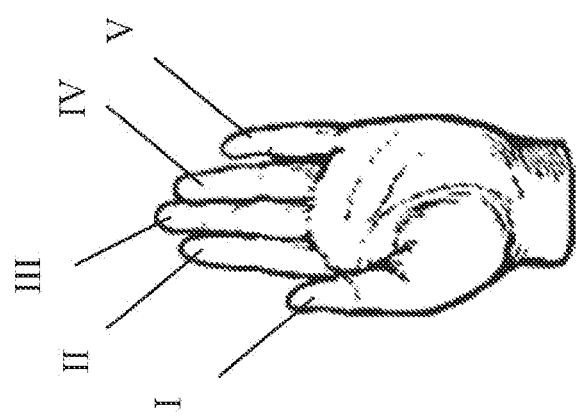
FIG. 7 illustrates average proportions of a human hand.

As used herein, the phrase "user length ratio" means an average proximal phalange length of a specific digit divided by the sum of an average distal phalange length of the specific digit added to an average intermediate phalange length of the specific digit, where the specific digit is designated as I, II, III, IV, and V at FIG. 7, and where the average proximal phalange length of the specific digit, the average distal phalange length of the specific digit, and the average intermediate phalange length of the specific digit is established according to the table at FIG. 7.

In operation, the plurality of calibration points will typically be generated by a user placing a palm on palm anchoring section 101 and moving a fingertip in contact with fingertip locator 102 to various locations, while fingertip locator 102 communicates with digital controller 103. As is understood, maintaining the user's finger substantially straight while the fingertip is moved to various locations improves the accuracy of the calibration. Similarly, maintaining the palm at a stationary position on palm anchoring section 101 while the fingertip is moved to various locations improves the accuracy of the calibration.

Having conducted the calibration procedure and thereby determined the location of user MCP joint 204, user proximal phalange length 206, and user intermediate-distal phalange length 207, digital controller 203 is programmed to read a specific fingertip location relative to fixed reference point P from fingertip locator 202 and determine the two MCP angles and the PIP angle necessary to achieve the specific fingertip location. The two MCP angles and the PIP angle determined generally reflect the posture of a user's finger such as finger 150 when achieving a specific fingertip location. Digital controller 203 communicates the two MCP angles and the PIP angle to data port 270.

Figure 3B:
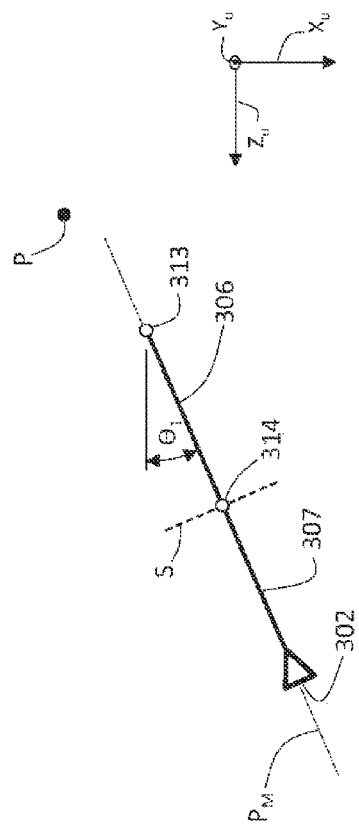
FIG. 3B illustrates a second view of the user planar linkage.

The digital controller determines the two MCP angles and the PIP angle by defining a user planar linkage comprised of a first link and a second link as illustrated at FIG. 3A. At FIG. 3A, the user planar linkage is comprised of first link 306 having a length equal to the user proximal phalange length determined during the calibration procedure. A first end of first link 306 is located at the location of the user MCP joint determined during the calibration procedure, and is anchored at the location of the user MCP joint by universal joint 313. Universal joint 313 has two 2 rotational degrees of freedom, where the first rotational degree of freedom is a rotation about user x-axis X, and the second rotational degree of freedom is a rotation about a user y-axis $Y_u$, and where the user x-axis $X_u$ is perpendicular to the user y-axis $Y_u$. A coordinate system illustrating the relationship between the user y-axis $Y_u$, the user x-axis $X_u$, and a user z-axis Z is included at FIG. 3A for reference, where the user x-axis $X_u$ proceeds out of the page, and where the user z-axis $Z_u$ is perpendicular to the user y-axis $Y_u$ and the user x-axis $X_u$. Additionally, a second end of the first link 306 is pinned at revolute joint 314. Revolute joint 314 is a single degree of freedom joint allowing rotation about a single rotation axis, where the single rotation axis is perpendicular to the user y-axis $Y_u$. For illustration, the user planar linkage is additionally indicated at FIG. 3B rotated 90°, as indicated by the coordinate system illustrating the user y-axis $Y_u$, the user x-axis $X_u$, and a user z-axis Z, where the user y-axis $Y_u$ proceeds out of the page. At FIG. 3B, revolute joint 314 allows rotation about the single rotation axis S, where single rotation axis S is perpendicular to the user y-axis $Y_u$.

The user planar linkage defined by the digital controller is further comprised of second link 307 having a length equal to the user intermediate-distal phalange length determined during the calibration procedure. A first end of second link 307 is pinned at revolute joint 314, and a second end of second link 307 is located at the specific fingertip location of fingertip locator 302. As a result of revolute joint 314 and universal joint 313, the user planar linkage comprised of first link 306 and second link 307 is constrained to motion in user linkage motion plane $P_M$, where user linkage motion plane $P_M$ is a single plane, and where the user y-axis $Y_u$ is either parallel to or residing within user linkage motion plane $P_M$, depending on where the origin of the $X_u$-$Y_u$-$Z_u$ coordinate system is located. At FIGS. 3A and 3B, the user linkage motion plane $P_M$ is a plane intersecting universal joint 313, first link 306, revolute joint 314, second link 307, and the specific fingertip location of fingertip locator 302, as illustrated.

Having defined the user planar linkage, the digital controller utilizes inverse kinematics on the 2 link, 3 degree of freedom user planar linkage to determine a first MCP angle, a second MCP angle, and a PIP angle necessary for fingertip locator 302 to attain the specific fingertip location reported. The first MCP angle is the angle between a user y-z plane and user linkage motion plane $P_M$, where the user y-z plane is defined by the user y-axis and the user z-axis. At FIG. 3B, the first MCP angle is illustrated as angle $\square_1$. The second MCP angle is the angle between first link 306 and a user x-z plane, where the user x-z plane is defined by the user x-axis and the user z-axis. At FIG. 3A, the second MCP angle is illustrated as angle $\square_2$. The PIP angle is the angle between first link 306 and second link 307, where the PIP angle is located within the user linkage motion plane. At FIG. 3A, the PIP angle is illustrated as angle $\square_3$.

The application of inverse kinematics to determine the first MCP angle, the second MCP angle, and the PIP angle as defined here for the 2 link, 3 degree of freedom planar linkage disclosed are well known in the art. See e.g., Sam Cubero, *Industrial Robotics: Theory, Modeling, and Control* (2006); see also S. K. Saha, *Introduction to Robotics* (2008); and see L. Sciavicco and B. Siciliano, *Modeling and Control of Robot Manipulators* (2005), among many others. The digital controller may be programmed to determine the specified angles using any analytical means known in the art. The digital programmer may make use of commercially available existing software packages to determine the specified angles, such as MATLAB available from The MathWorks Inc., Nattick, Mass., USA; MATHEMATICA available from Wolfram-Alpha LLC Champaign, Ill., USA, and others. The specific means by which the digital controller determines the first MCP angle $\square_1$, the second MCP angle $\square_2$, and the PIP angle $\square_3$ using inverse kinematics is not limiting within this disclosure, provided that the digital controller defines the user planar linkage comprised of universal joint 313, first link 306, revolute joint 314, and second link 307 based on parameters determined using the specified calibration procedure, and executes the reverse kinematics to achieve the specific fingertip location indicated by fingertip locator 302. Additionally, in determining the PIP angle $\square_3$ using the inverse kinematics, the digital controller constrains solutions to those which indicate a value for the PIP angle $\square_3$ achievable by a normally functioning human finger.

Utilizing inverse kinematics to determine the first MCP angle, the second MCP angle, and the PIP angle for the 2 link, 3 degree of freedom planar linkage as described allows the user interface to approximate the angular positions of a user's fingers/thumb without the adverse consequences of direct measurement approaches, such as having one's finger movement restricted by a glove, and having to carry the weight of such a device.

Figure 4:
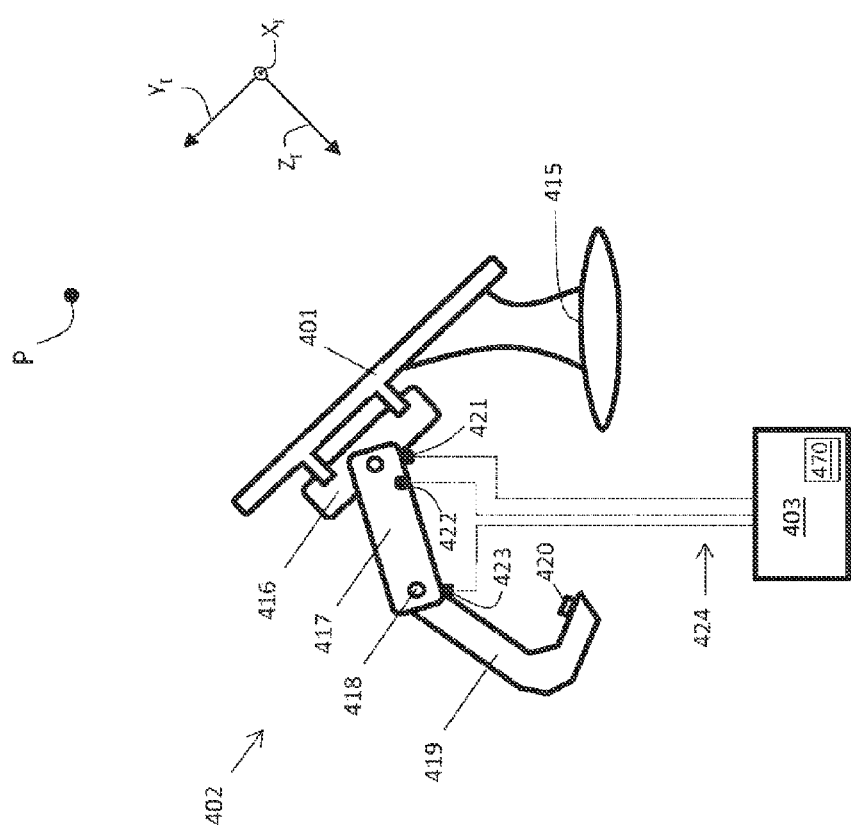
FIG. 4 illustrates an embodiment of a fingertip locator.

A specific embodiment of a user interface is illustrated at FIG. 4, and is comprised of a fingertip locator generally indicated at 402. The user interface is comprised of 2 DOF interface universal joint 416, first serial linkage 417, interface revolute joint 418, second serial linkage 419, user end-effector 420, palm anchoring section 401, digital controller 403, and other components. At FIG. 4, 2 DOF interface universal joint 416 has two 2 rotational degrees of freedom, where the first rotational degree of freedom is a rotation about interface x-axis $X_I$ and the second rotational degree of freedom is a rotation about a interface y-axis $Y_I$, and where the interface x-axis $X_I$ is perpendicular to the interface y-axis $Y_I$. A coordinate system illustrating the relationship between the interface y-axis $Y_I$, the interface x-axis $X_I$, and an interface z-axis $Z_I$ is included at FIG. 4 for reference, where the interface x-axis $X_I$ proceeds out of the page, and where the interface z-axis $Z_I$ is perpendicular to the interface y-axis $Y_I$ and the interface x-axis $X_I$. Such 2 DOF interface universal joints are known in the art and may be typically termed simply a universal joint, a Hooke joint, a Cardan joint, or other terms. See e.g, B. Siciliano and O. Khatib, *Springer Handbook of Robotics* (2008), among many others.

First serial linkage 417 is a rigid link, where a first end of first serial linkage 417 is anchored by 2 DOF interface universal joint 416. A second end of the first serial linkage 417 is pinned at interface revolute joint 418, and a first linkage length is equal to the displacement from the first end of first serial linkage 417 to the second end of first serial linkage 417.

Interface revolute joint 418 is a single degree of freedom joint allowing rotation about a single joint rotation axis, where the single joint rotation axis is perpendicular to the interface y-axis $Y_I$. The relationship between the single joint rotation axis of interface revolute joint 418 and the interface y-axis $Y_I$ is similar to the relationship between single rotation axis S and the user y-axis $Y_u$ discussed earlier. Such revolute joints are similarly known in the art. See e.g, B. Siciliano and O. Khatib, among others.

Second serial linkage 419 is a rigid link, where a first end of second serial linkage 419 is pinned at interface revolute joint 418. A second end of second serial linkage 419 is attached to user end-effector 420. A first linkage length is equal to the displacement from the first end of second serial linkage 419 to user end-effector 420. As a result of interface revolute joint 418 and universal joint 416, an interface planar linkage comprised of first serial linkage 417 and second serial linkage 419 is constrained to motion in an interface linkage motion plane (not shown), where the interface linkage motion plane is a single plane, and where the interface y-axis $Y_I$ is either parallel to or residing within the interface linkage motion plane, depending on where the origin of the $X_I$-$Y_I$-$Z_I$ coordinate system is located. At FIG. 4, the interface linkage motion plane is a plane intersecting 2 DOF interface universal joint 416, first serial linkage 417, interface revolute joint 418, second serial linkage 419, and user end-effector 420.

User end-effector 420 is a body fixably attached to the second end of second serial linkage 419. In operation, user end-effector 420 is intended to remain in contact with the fingertip of a user's finger. Some ways to achieve reliable contact between the user's fingertip and the end-effector include, but are not limited to, a magnetic base with a steel sphere attached to the user's fingertip or a Velcro strap.

Fingertip locator 402 is further comprised of a first joint angle sensor 421. First joint angle sensor 421 provides indications allowing determination of a first angle, where the first angle is an angle between an interface y-z plane and the interface linkage motion plane, where the interface y-z plane is defined by the interface y-axis $Y_I$ and the interface z-axis $Z_I$. Fingertip locator 402 is additionally comprised of second joint angle sensor 422. Second joint angle sensor 422 provides indications allowing determination of a second angle, where the second angle is an angle between first serial linkage 417 and an interface x-z plane, where the interface x-z plane is defined by the interface x-axis $X_I$ and the interface z-axis $Z_I$. Fingertip locator 402 is additionally comprised of third joint angle sensor 423. Third joint angle sensor 423 provides indications allowing determination of a third angle, where the third angle is a joint angle between the first serial linkage 417 and the second serial linkage 419 in the interface linkage motion plane. First angle sensor 421, second angle sensor 422, and third angle sensor 423 may be any means known for determining the angles as described. The angle sensors may be devices typically known as goniometers, and may operate as electro-mechanical devices, optical flex devices, strain sensing devices, or other means. See e.g., U.S. Pat. No. 4,442,606 to Graham et al., U.S. Pat. No. 6,983,547 to Fleming et al., U.S. Pat. No. 5,792,077 Gomes, U.S. Pat. No. 5,442,729 to Kramer et al., U.S. Pat. No. 6,035,274 to Kramer et al. U.S. Pat. No. 5,086,785 to Gentile et al., U.S. Pat. No. 4,542,291 to Zimmerman, among others.

Fingertip locator 402 is fixably attached to palm anchoring section 401 at 2 DOF interface universal joint 416. Palm anchoring section 401 is additionally comprised of palm anchoring surface 415. Palm anchoring surface 415 is intended to support the palm of a user while the user's fingertip is in contact with user end-effector 420. Correspondingly, palm anchoring surface 415 is located on palm anchoring section 401 and has an orientation to 2 DOF interface universal joint 416 such that the interface planar linkage comprised of first serial linkage 417 and second serial linkage 419 can rotate about the interface x-axis $X_I$ to a position where end-effector 420 is within at least 200 millimeters of palm anchoring surface 415.

Further at FIG. 4, first angle sensor 421, second angle sensor 422, and third angle sensor 423 are in data communication with digital controller 403, as generally indicated at 424. Digital controller 403 is additionally comprised of data port 470. In this embodiment, digital controller 403 communicates with first joint angle sensor 421 and receives indications allowing determination of the first angle, communicates with second joint angle sensor 422 and receives indications allowing determination of the second angle, communicates with third joint angle sensor 423 and receives indications allowing determination of the third angle, and determines the specific fingertip location corresponding to the location of user end-effector 420 using forward kinematics of the 2 link, 3 degree of freedom interface planar linkage comprising fingertip locator 402. The application of forward kinematics to a 2 link, 3 degree of freedom planar linkage in order to determine the location of an end-effector is well known in the art. See e.g., Cubero; see also S. K. Saha; see also L. Sciavicco and B. Siciliano, among many others.

An advantage of the fingertip locator of FIG. 4 is that a user's hand may operate via a structure that allows a user's hand to be comfortably positioned and secured in space. In an embodiment, palm anchoring section 401 is comprised of additional structure which acts to firmly hold a user's palm on palm anchoring surface 415 in substantially the same location, so that user MCP joint defined during the calibration procedure remains in substantially the same position during use. For example, palm anchoring section 401 may incorporate straps, surface contouring, or other means to assist in maintaining a substantially stationary position. In an embodiment, palm anchoring section 401 is comprised of an inflatable bladder which inflates to gently press against the back of the user's hand, securing the user's hand against palm anchoring surface 415.

The user interface may be further comprised of a plurality of fingertip locators, where each fingertip locator in the plurality is in data communication with the digital controller, and where the digital controller is configured to conduct the calibration procedure for each individual fingertip locator in order to determine an individual MCP joint location, an individual proximal phalange length, and individual intermediate-distal phalange length of the individual user finger in contact with the each individual fingertip locator. When the user interface is comprised of the plurality of fingertip locators, the digital controller receives individual specific fingertip locations from each fingertip locator and conducts reverse kinematics using at least the individual specific fingertip location, the individual MCP joint location, the individual proximal phalange length, and the individual intermediate-distal phalange length. Additionally, in an embodiment, an individual user length ratio $L_{P-AVG}/(L_{D-AVG}+L_{I-AVG})$ or $L_{M-AVG}/(L_{P-AVG}+L_{D-AVG})$ is separately determined for each individual user finger in contact with a individual fingertip locator, and in each case an individual first length divided by an individual second length is within 10% of the individual user length ratio for the specific digit representing the individual user finger at FIG. 7, and preferably equal to the individual user length ratio.

Figure 5:
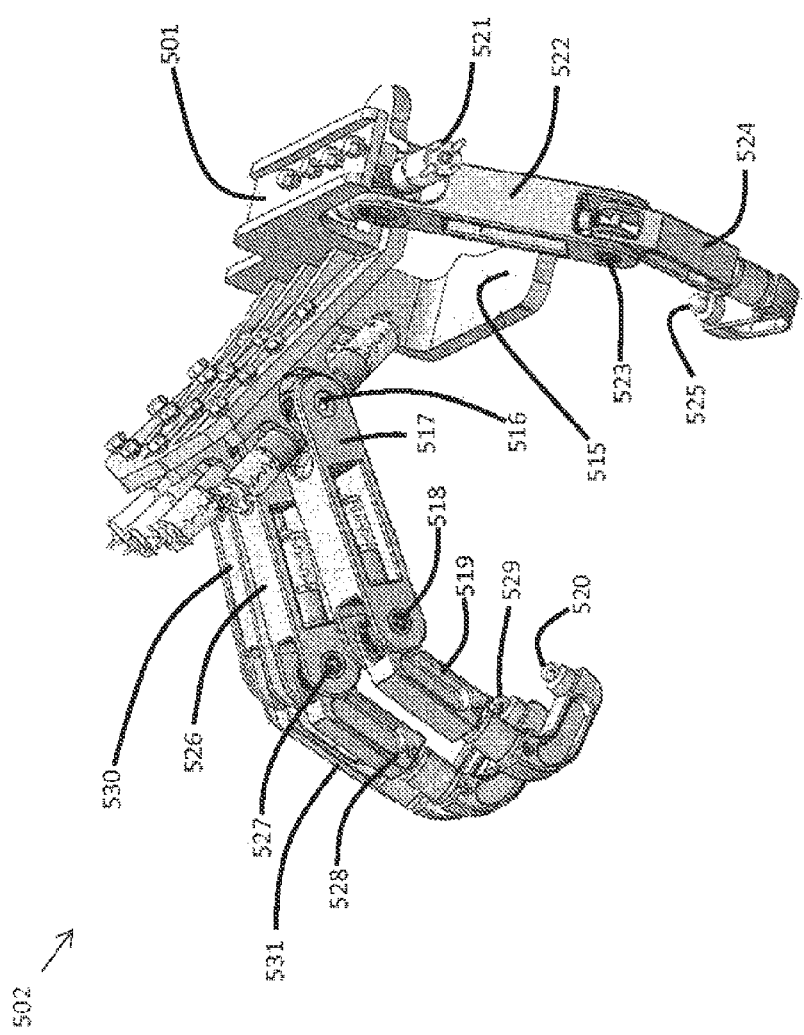
FIG. 5 illustrates a second embodiment of a fingertip locator.

As an example, FIG. 5 illustrates a generally isometric view of a user interface indicated generally at 502 and comprised of a plurality of fingertip locators. FIG. 5 illustrates palm anchoring surface comprising palm anchoring section 501. A first fingertip locator is comprised of 2 DOF interface universal joint 516 fixably attached to palm anchoring section 501, first serial linkage 517 is rotatably attached to universal joint 516 and interface revolute joint 518, and second serial linkage 519 rotatably attached to interface revolute joint 518 and terminating at user end-effector 520. In addition, a second fingertip locator is comprised of 2 DOF interface universal joint 521 fixably attached to palm anchoring section 501, first serial linkage 522 is rotatably attached to universal joint 521 and interface revolute joint 523, and second serial linkage 524 rotatably attached to interface revolute joint 523 and terminating at user end-effector 525. A third finger locator is partially viewable, and is comprised of first serial linkage 526 rotatably attached to interface revolute joint 527 and a universal joint fixably attached to palm anchoring section 501, and second serial linkage 528 rotatably attached to interface revolute joint 527 and terminating at user end-effector 529. A fourth finger locator is also partially viewable, comprised of first serial linkage 530 and second serial linkage 531.

Figure 6:
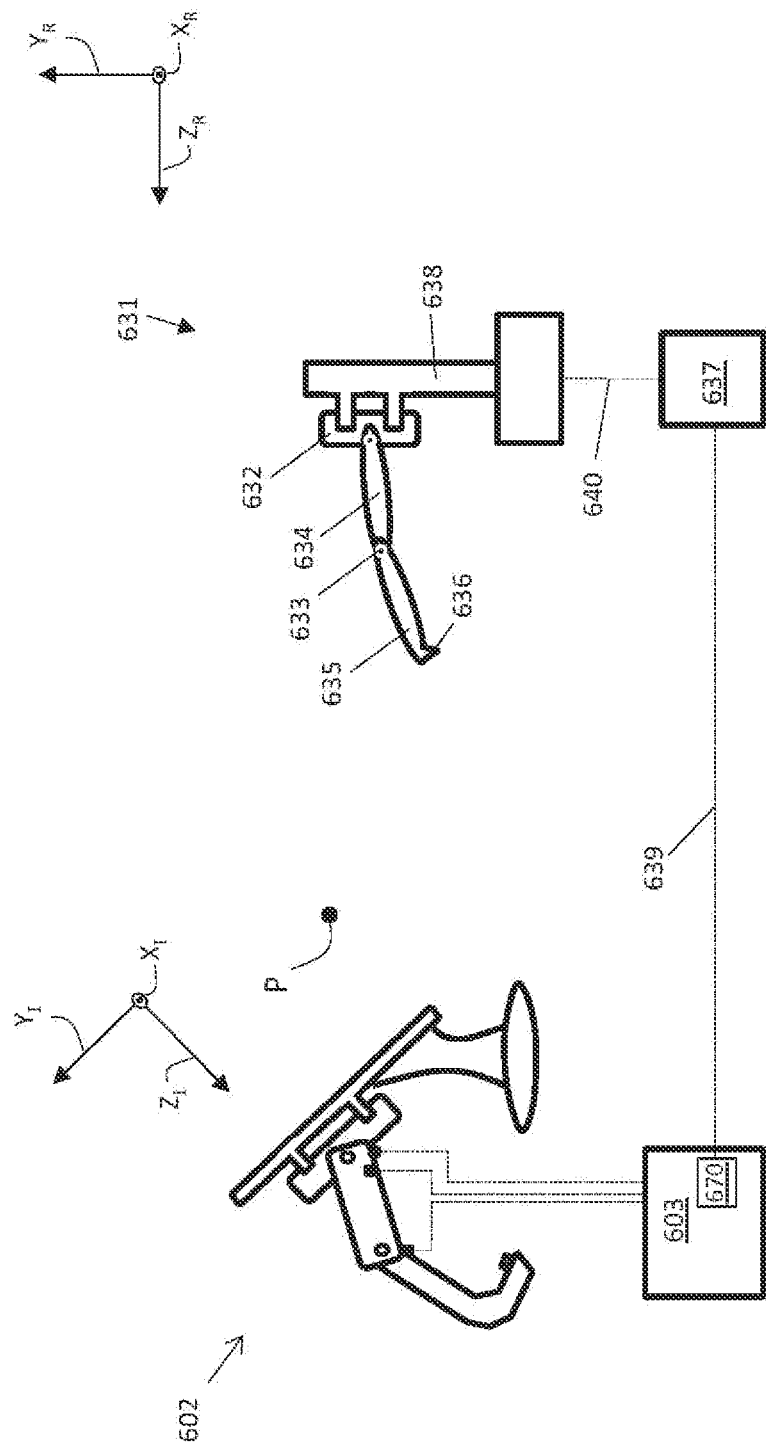
FIG. 6 illustrates a fingertip locator and a specific robotic hand.

In an embodiment, the user interface communicates information describing the first MCP angle, the second MCP angle and the PIP angle to a robotic hand comprised of a robotic controller and at least one robotic finger, where the robotic finger is comprised of a robotic MCP joint, a robotic PIP joint, a robotic proximal phalange, and a robotic intermediate-distal phalange. For example, FIG. 6 illustrates a user interface 602 comprised of digital controller 603. Digital controller 603 determines a first MCP angle, a second MCP angle, and a PIP angle based on the specific location of the user end-effector of user interface 602 and using fixed reference point P and the $X_I$-$Y_I$-$Z_I$ axes indicated as before, and is further in data communication with a robotic hand generally indicated at 631. Digital controller 603 communicates information describing the first MCP angle, the second MCP angle and the PIP angle through data port 670 via pathway 639 to robotic controller 637, which is in data communication with robotic hand 631 via pathway 640. Robotic hand 631 is comprised of robotic MCP joint 632 is fixably attached to robotic support structure 638, where robotic MCP joint 632 has at least a first robotic rotational degree of freedom around an x-axis $X_R$ and a second robotic rotational degree of freedom around a y-axis $Y_R$, where $X_R$ and $Y_R$ are perpendicular. This is illustrated by the coordinate axes at FIG. 6 with the x-axis $X_R$ coming out of the page, and a z-axis $Z_R$ perpendicular to both $X_R$ and $Y_R$. Robotic hand 631 is further comprised of robotic PIP joint 633 having at least one rotational degree of freedom around a robotic joint rotation axis, where the robotic joint rotation axis is perpendicular to the robotic y-axis $Y_R$. Robotic hand 631 is further comprised of robotic proximal phalange 634, where a first end of robotic proximal phalange 634 is anchored by robotic MCP joint 632 and a second end of robotic proximal phalange 634 is pinned at robotic PIP joint 633, and further comprised of a robotic intermediate-distal phalange 635 having a first end pinned at robotic PIP joint 633 and a second end attached to a robotic end-effector 636.

In an embodiment, the robotic phalange lengths comprising robotic hand 631 mimic the average proportions of a digit of a human hand. In this embodiment, a robotic proximal phalange length $L_{R-P}$ is the displacement between the first and second end of robotic proximal phalange 634, and a robotic intermediate-distal phalange length $L_{R-I}$ is the displacement between the first end of robotic intermediate-distal phalange 635 and robotic end-effector 636. A robotic length ratio $L_{R-P}/L_{R-I}$ is equal to robotic proximal phalange length $L_{R-P}$ divided by the robotic intermediate-distal phalange length $L_{R-P}$. In this embodiment, the robotic length ratio $L_{R-P}/L_{R-I}$ is within 10% of a user length ratio for a specific digit illustrated at FIG. 7, such that the robotic length ratio $L_{R-P}/L_{R-I}$ divided by the user length ratio for the specific digit is greater than or equal to 0.9 and less than or equal to 1.1. Typically, the user length ratio for the specific digit corresponds to the finger of a user's hand anticipated to be used for operating user interface 602.

In an embodiment, robotic proximal phalange 634 and the robotic intermediate-distal phalange 635 comprise a robotic planar linkage having motion within a robotic linkage motion plane, where the robotic y-axis $Y_R$ resides in the robotic linkage motion plane. In this embodiment, robotic hand 631 is further comprised of a first joint positioning means connected to robotic proximal phlange 634 for establishing a first robotic MCP angle, and where the first robotic MCP angle is the angle between a robotic y-z plane and the and the robotic linkage motion plane, where the robotic y-z plane is defined by the robotic y-axis $Y_R$ and robotic z-axis $Z_R$. Robotic hand 631 is further comprised of a second joint positioning means for establishing a second robotic MCP angle. The second joint positioning means is connected to robotic proximal phlange 634 and robotic intermediate-distal phalange 635, and the second robotic MCP angle is an angle between robotic proximal phlange 634 and the robotic x-z plane, where the robotic x-z plane is defined by the robotic x-axis $X_R$ and the robotic z-axis $Z_R$. Robotic hand 631 is further comprised of a third joint positioning means for establishing a robotic PIP angle, where the robotic PIP angle is a joint angle between robotic proximal phlange 634 and robotic intermediate-distal phalange 635 in the robotic linkage motion plane. Further, the first joint positioning means, the second joint positioning means, and the third joint positioning means are in data communication with robotic controller 637. In this embodiment, digital controller 603 receives indications of a specific fingertip location from a user interface such as user interface 602, determines a first MCP angle, a second MCP angle, and a PIP angle based on the specific fingertip location and user MCP location, the user proximal phalange length, and the user intermediate-distal phalange length determined during the calibration procedure, and communicates the first MCP angle, the second MCP angle, and the PIP angle to robotic controller 637. Robotic controller 637 then communicates the first MCP angle to the first joint positioning means, the second MCP angle to the second joint positioning means, and the PIP angle to the third joint positioning means. The first joint positioning means, the second joint positioning means, and the third joint positioning means then establish the first MCP angle, the second MCP angle, and the PIP angle respectively, resulting in robotic hand 631 assuming a posture similar to a user's finger in contact with user end-effector 602.

Such joint positioning means as discussed above are known in the art. See e.g., U.S. Pat. No. 8,052,185 to Madhani, filed Apr. 9, 2009, issued Nov. 8, 2011; see also U.S. Pat. No. 5,062,673 to Mimura, filed Dec. 28, 1989, issued Nov. 5, 1991; see also U.S. Pat. No. 5,437,490 to Mimura, filed May 18, 1994, issued Aug. 1, 1995; see also U.S. Pat. No. 7,370,896 to Anderson et al., filed Dec. 20, 2004, issued May 13, 2008; and see U.S. Pat. No. 6,247,738 to Winkel et al., filed Jan. 20, 1998, issued Jun. 19, 2001, among others.

Robotic controller 637 may also provide force feedback to digital controller 603, by sensing a force experienced by robotic hand 631 and communicating with digital controller 603 such that a representative force is reflected back on the user. User interface 602 may be various haptic devices for such force feedback, including impedance-type and admittance-type devices. See e.g Crawford et al., "Force Control and Non-linear Master-Slave Force Profile to Manage and Admittance Type Multi-fingered Haptic User Interface," Resilient Control Systems (ISRCS), 2012 5th International Symposium on (2012); see also Crawford et al, "Nonlinear Force Profile Used to Increase the Performance of a Haptic User Interface for Teleoperating a Robotic Hand," (INL/CON-11-23691) Idaho National Laboratory (2012) (OSTI ID: 1054298).

In an embodiment, the user interface is rotatably attached to a wrist assembly comprised of a supination/pronation joint, an extension/flexion joint, and a radial ulnar joint. The radial ulnar joint has a single rotational degree of freedom about a radial/ulnar axis, where the radial/ulnar axis is parallel to or resides within the user y-z plane defined by interface y-axis $Y_I$ and interface z-axis $Z_I$. The extension/flexion joint has a single rotational degree of freedom about an extension/flexion axis, where the extension/flexion axis is perpendicular to the radial/ulnar axis, in order to mimic the rotations of a human wrist. The supination/pronation joint has a single rotational degree of freedom about a supination/pronation axis, where the supination pronation axis is perpendicular to the extension/flexion axis and perpendicular to the radial/ulnar axis. In a further embodiment, the wrist assembly has a lateral degree of freedom along each of the interface x-axis $X_I$, the interface y-axis $Y_I$, and the interface z-axis $Z_I$.

Figure 8:
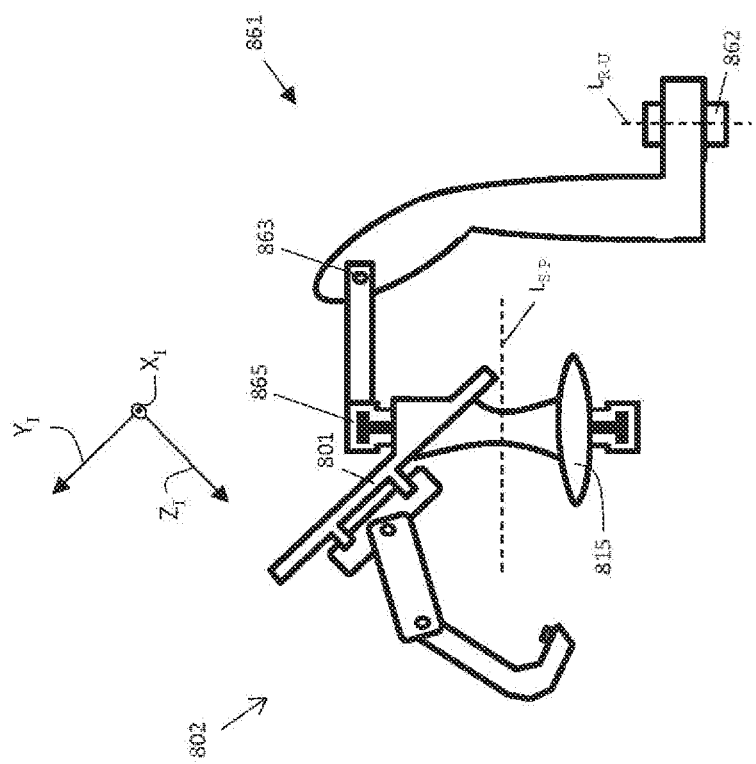
FIG. 8 illustrates a further embodiment of the user interface.
Figure 9:
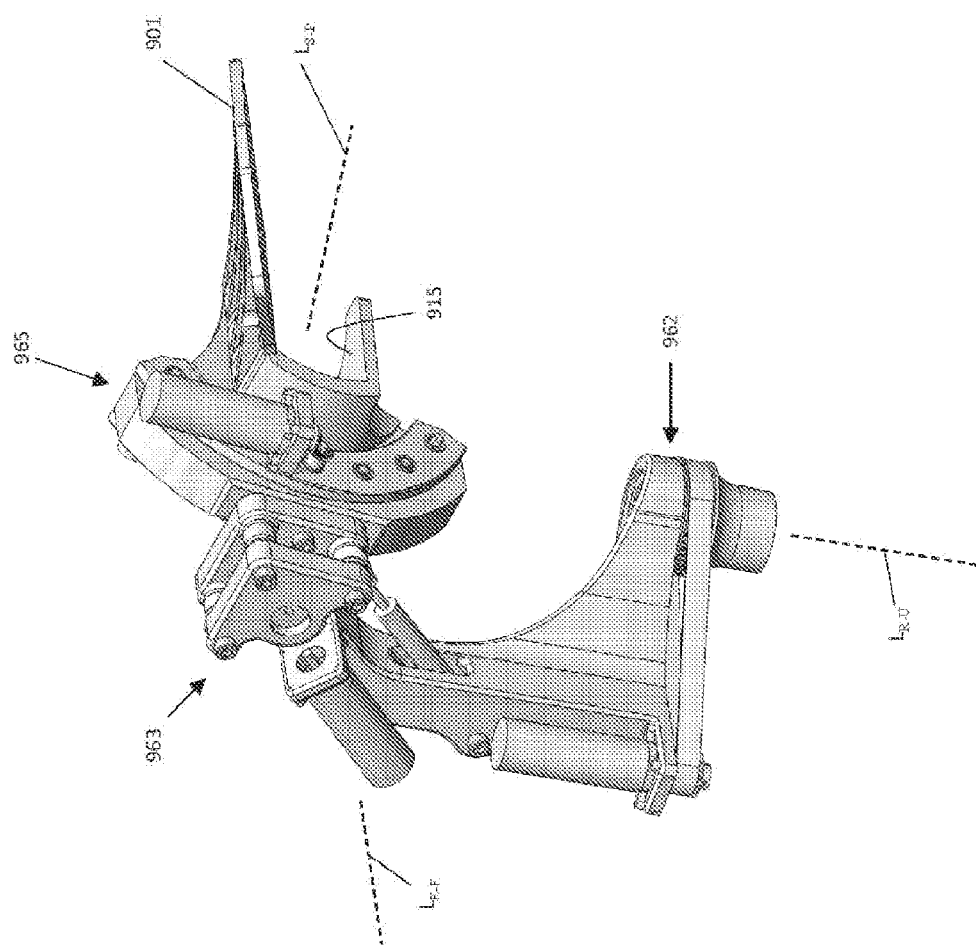
FIG. 9 illustrates an embodiment of a wrist assembly.

An embodiment of the wrist assembly generally indicated at 861 is illustrated at FIG. 8. FIG. 8 illustrates a user interface 802 comprised of palm anchoring section 801 with palm anchoring surface 815 and constructed relative to the interface x-axis $X_I$, the interface y-axis $Y_I$, and the interface z-axis $Z_I$ axes shown. User interface 802 is attached to wrist assembly 861 at supination/pronation joint 865, where supination/pronation joint 865 has a single rotational degree of freedom about supination/pronation axis $L_{S-P}$. Supination/pronation joint 865 is attached to extension/flexion joint 863, where extension/flexion joint 863 has a single rotational degree of freedom about an extension/flexion axis. Supination/pronation joint 865 is attached to radial/ulnar joint 862, where radial/ulnar joint 862 has a single rotational degree of freedom about radial/ulnar axis $L_{R-U}$. Radial/ulnar axis $L_{R-U}$ is parallel to or resides within the user y-z plane defined by interface y-axis $Y_I$ and interface z-axis $Z_I$, the extension/flexion axis is perpendicular to radial/ulnar axis $L_{R-U}$, and supination pronation axis $L_{S-P}$ is perpendicular to the extension/flexion axis and perpendicular to radial/ulnar axis $L_{R-U}$. Additionally, radial/ulnar joint 862 has of wrist assembly 861 has a lateral degree of freedom along each of the interface x-axis $X_I$, the interface y-axis $Y_I$, and the interface z-axis $Z_I$. Another embodiment is isometrically illustrated at FIG. 9. FIG. 9 indicates the palm anchoring section 901 of a user interface attached to a supination/pronation joint generally indicated at 965 and having rotational freedom about supination/pronation axis $L_{S-P}$, where supination/pronation joint 965 is attached to an extension/flexion joint generally indicated at 963 and having rotational freedom about an extension/flexion axis $L_{E-F}$, and where extension/flexion joint 963 is attached to a radial/ulnar joint generally indicated at 962 and having rotational freedom about radial/ulnar axis $L_{R-U}$. At FIG. 9, the extension/flexion axis $L_{E-F}$ is perpendicular to radial/ulnar axis $L_{R\text{-}U}$, and supination pronation axis $L_{S\text{-}P}$ is perpendicular to extension/flexion axis $L_{E\text{-}F}$ and perpendicular to radial/ulnar axis $L_{R\text{-}U}$.

Figure 10:
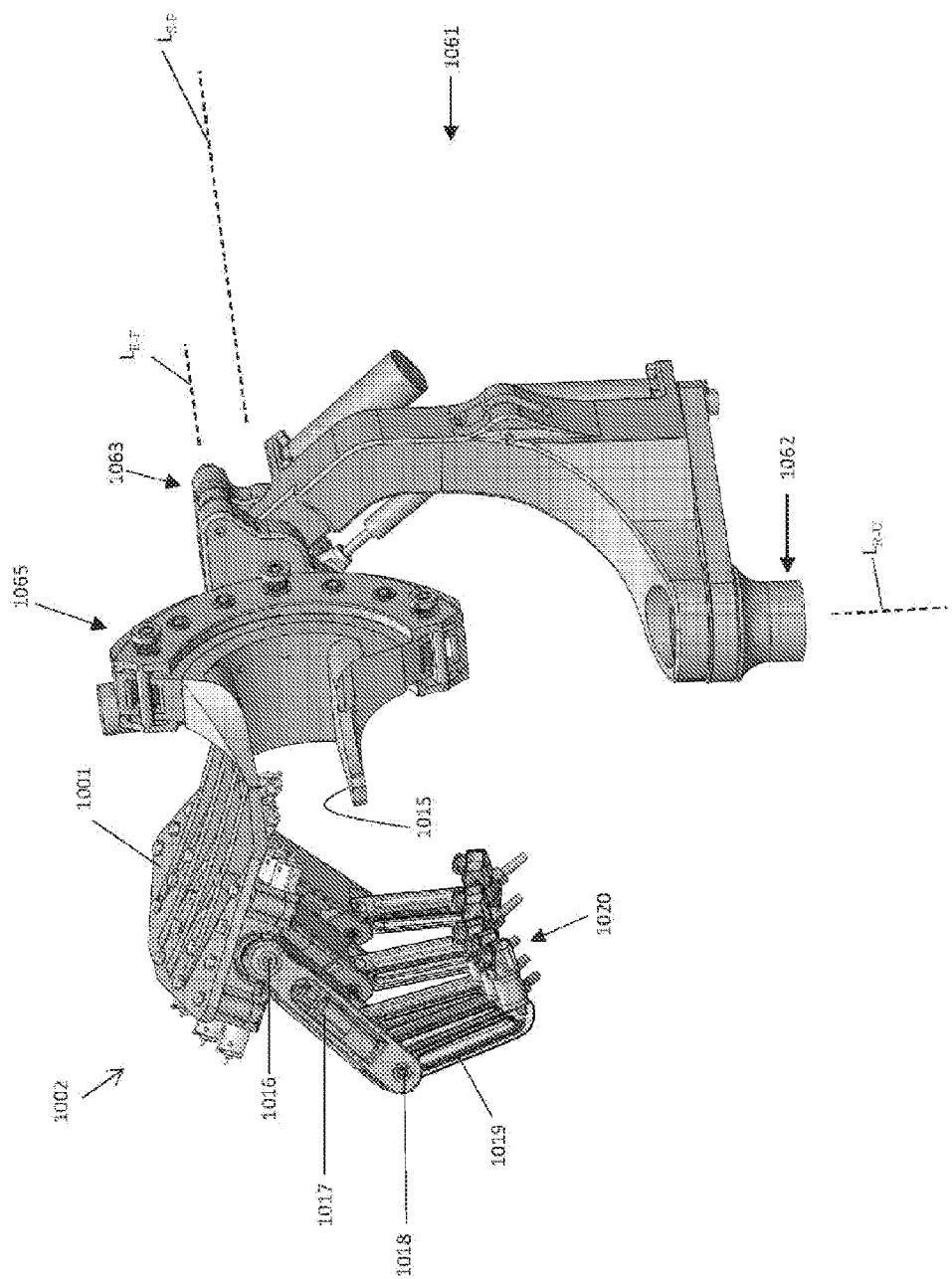
FIG. 10. illustrates an embodiment of a user interface with a wrist assembly.

An additional embodiment showing a user interface generally indicated at 1002 and a wrist assembly generally indicated at 1061 is isometrically illustrated at FIG. 10. User interface 1002 is comprised palm anchoring surface 1015 and additionally comprised of a plurality of fingertip locators, including a first fingertip locator comprised of 2 DOF interface universal joint 1016 fixably attached to palm anchoring section 1001, first serial linkage 1017 rotatably attached to universal joint 1016 and interface revolute joint 1018, and second serial linkage 1019 rotatably attached to interface revolute joint 1018 and terminating at user end-effector 1020. Additionally, palm anchoring section 1001 is attached to a supination/pronation joint generally indicated at 1065 and having rotational freedom about supination/pronation axis $L_{S\text{-}P}$, and supination/pronation joint 1065 is attached to an extension/flexion joint generally indicated at 1063 and having rotational freedom about an extension/flexion axis $L_{E\text{-}F}$, and extension/flexion joint 1063 is attached to a radial/ulnar joint generally indicated at 1062 and having rotational freedom about radial/ulnar axis $L_{R\text{-}U}$. At FIG. 10, the extension/flexion axis $L_{E\text{-}F}$ is perpendicular to radial/ulnar axis $L_{R\text{-}U}$, and supination pronation axis $L_{S\text{-}P}$ is perpendicular to extension/flexion axis $L_{E\text{-}F}$ and perpendicular to radial/ulnar axis $L_{R\text{-}U}$. Note that user interface 1002 differs slightly from user interface 502 in that the fingertip locators for all five fingers including a thumb are positioned in substantially adjacent positions relative to the palm anchoring surface.

In an embodiment, the user interface is further comprised of a means to determine a user wrist location, a user forearm length, and a user arm length, where the user forearm length refers to the distance between a user's elbow and a user's wrist, and where the user arm length refers to the distance between a user's shoulder and a user's elbow. The user wrist location is defined relative to a stationary reference point, which may or may not be the fixed reference point P. The means for determining the user wrist location relative to the stationary reference point may be any means, for example, a linkage connected between the wrist assembly and a stationary anchor point, a visual marker system, an electromagnetic tracking system, or any others system sufficient for reporting the wrist location with respect to a fixed reference point.

In this embodiment, the digital controller is further programmed to determine the user forearm length from a plurality of specific wrist locations. The specific wrist locations are treated as forearm calibration points and utilized to determine the center of a forearm calibration sphere, in a manner similar to the method utilized to determine the center of the calibration sphere from the plurality of calibration points, as discussed earlier. In operation, the plurality of forearm calibration points is obtained by a user maintaining an elbow position substantially constant and moving the wrist to a series of locations. The center of the forearm calibration sphere is determined from the plurality of forearm calibration points, and the user forearm length is defined as the radius of the forearm calibration sphere.

Similarly, in this embodiment, the digital controller is further programmed to determine the user arm length from a plurality of specific wrist locations. The specific wrist locations are treated as arm calibration points and utilized to determine the center of an arm calibration sphere, in a manner similar to the method utilize to determine the center of the calibration sphere from the plurality of calibration points, as discussed earlier. In operation, the plurality of arm calibration points is obtained by a user maintaining a shoulder position substantially constant, maintaining a substantially straight arm posture, and moving the wrist to a series of locations. The center of the arm calibration sphere is determined from the plurality of arm calibration points, and the user arm length is defined as the radius of the arm calibration sphere minus the radius of the forearm calibration sphere.

In this embodiment, with a defined wrist location, a user forearm length, and a user arm length, the digital controller may treat the user forearm length and the user arm length as a planar linkage and determine descriptive angles describing the posture of a user's forearm and arm necessary to achieve a specific wrist location during operation using reverse kinematics, in a manner similar to that described for determination of the first MCP angle, the second MCP angle, and the PIP angle.

The user interface may be operated by placing a user's palm in contact with the palm anchoring section and placing a fingertip of a user's finger in contact with the fingertip locator, then positioning the fingertip of the user's finger at a calibration point while maintaining the user's finger is a substantially straight position and allowing the fingertip locator to communicate data to the digital controller. The digital controller is permitted to evaluate the data communicated and generate a calibration point location. This is repeated until a plurality of calibration point locations is generated. Using the plurality of calibration points, the digital controller defines the calibration sphere center location relative to the fixed reference point and establishes the user MCP joint location at the calibration sphere center location. The digital controller further determines the user finger length based on the radius of the calibration sphere, and establishes the user proximal phalange length equal and user intermediate-distal phalange length.

Following the calibration procedure, the user interface may be utilized to manipulate a robotic hand by placing the user's palm in contact with the palm anchoring section, placing a fingertip of a user's finger in contact with the fingertip locator, and positioning the fingertip locator. The fingertip locator communicates data to the digital controller, and the digital controller generates a specific fingertip location. Based on the specific fingertip location, the digital controller defines the user planar linkage comprised of a first link and a second link, and determines the first MCP angle, the second MCP angle, and the PIP angle for the specific fingertip location. The digital controller communicates information defining the first MCP angle, the second MCP angle, and the PIP angle to the robotic hand controller, and the robotic hand controller communicates the first MCP angle to a first joint positioning means, communicates the second MCP angle to a second joint positioning means, and communicates the PIP angle to a third joint positioning means.

Thus disclosed here is a user interface for a robotic hand intended to monitor and discern the posture of a user's hand during typical grasping and manipulation motions, based on tracking the locations of the user's fingertips relative to some fixed reference point. The user interface substantially anchors a user's palm in a relatively stationary position, and relays various angles of interest to a robotic hand having substantially the same configuration and proportions. The user interface acts to anchor the user's palm in a relatively stationary position and orientation, conducts a calibration procedure to determine the user's applicable physiological dimensions, and determines MCP and PIP angles of interest necessary to achieve the specific fingertip location. The user interface communicates the respective angles to a gripping-type end effector which closely mimics the user's available range of motion and a typical human proportion. The user interface requires minimal contact with the operator, allows for a wide working space and range of motions, and provides distinct advantages in terms of available dexterity, work space flexibility, and adaptability to different users.

It is to be understood that the above-described arrangements are only illustrative of the application of the principles of the present invention and it is not intended to be exhaustive or limit the invention to the precise form disclosed. Numerous modifications and alternative arrangements may be devised by those skilled in the art in light of the above teachings without departing from the spirit and scope of the present invention. It is intended that the scope of the invention be defined by the claims appended hereto.

In addition, the previously described versions of the present invention have many advantages, including but not limited to those described above. However, the invention does not require that all advantages and aspects be incorporated into every embodiment of the present invention.

All publications and patent documents cited in this application are incorporated by reference in their entirety for all purposes to the same extent as if each individual publication or patent document were so individually denoted.

What is claimed is:

1. A user interface for determining a first MCP angle, a second MCP angle, and a PIP angle, where MCP denotes metacarpophalangeal and where PIP denotes proximal interphalangeal, comprising:
   a fingertip locator, where the fingertip locator defines a location relative to a fixed reference point;
   a palm anchoring section; and
   a digital controller in data communication with the fingertip locator, where the digital controller is comprised of a data port, and where the digital controller is programmed for,
      conducting a calibration procedure and determining a user MCP joint location relative to the fixed reference point, a user proximal phalange length, and a user intermediate-distal phalange length by,
         receiving a plurality of calibration point locations from the fingertip locator, where each calibration point location in the plurality of calibration point locations has a unique location relative to the fixed reference point, and where a quantity of calibration point locations in the plurality of calibration point locations is equal to at least four,
      defining a center of a calibration sphere using the plurality of calibration point locations, and determining a calibration sphere radius of the calibration sphere,
      establishing the user MCP joint location at the center of the calibration sphere, thereby determining the user MCP joint location relative to the fixed reference point and,
      determining a user finger length based on the calibration sphere radius, and dividing the user finger length into a first length and a second length based on the user finger length, and establishing the user proximal phalange length equal to the first length and establishing the user intermediate-distal phalange length equal to the second length, thereby determining the user proximal phalange length and the user intermediate-distal phalange length, and thereby conducting the calibration procedure and,
   determining the first MCP angle, the second MCP angle, and the PIP angle by,
      reading a specific fingertip location relative to the fixed reference point from the fingertip locator;
      defining a user planar linkage comprised of,
         a first link, where a displacement from a first end of the first link to a second end of the first link is equal to the user proximal phalange length, and where the first end of the first link is located at the user MCP joint location and anchored by a 2 DOF universal joint, where the 2 DOF universal joint has a first rotational degree of freedom and a second rotational degree of freedom, where the first rotational degree of freedom is a rotation about a user x-axis and where the second rotational degree of freedom is a rotation about a user y-axis, where the user x-axis is perpendicular to the user y-axis, and where the second end of the first link is pinned at a revolute joint, where the revolute joint is a single degree of freedom joint allowing rotation about a single rotation axis, where the single rotation axis is perpendicular to the user y-axis and,
         a second link, where a displacement from a first end of the second link to a second end of the second link is equal to the user intermediate-distal phalange length, and where the second end of the second link is located at the specific fingertip location, and where the first end of the second link is pinned at the revolute joint, such that the user planar linkage has motion constrained to a user linkage motion plane, where the user y-axis resides in or is parallel to the user linkage motion plane and,
      defining the first MCP angle, the second MCP angle, and the PIP angle for the specific fingertip location using inverse kinematics and the user planar linkage, where the first MCP angle is an angle between a user y-z plane and the user linkage motion plane, where the user y-z plane is defined by the user y-axis and a user z-axis, where the user z-axis is perpendicular to the user x-axis and perpendicular to the user y-axis, and where the second MCP angle is an angle between the first link and a user x-z plane, where the user x-z plane is defined by the user x-axis and the user z-axis, and where the PIP angle is a joint angle between the first link and the second link in the user linkage motion plane, thereby determining the first MCP angle, the second MCP angle, and the PIP angle and,
      communicating the first MCP angle, the second MCP angle, and the PIP angle through the data port.

2. The user finger interface of claim 1 where the fingertip locator is comprised of;
   a 2 DOF interface universal joint fixably attached to the palm anchoring section, where the 2 DOF interface universal joint has a first joint rotational degree of freedom and a second joint rotational degree of freedom, where the first joint rotational degree of freedom is a rotation about an interface x-axis and where the second joint rotational degree of freedom is a rotation about an interface y-axis, where the interface x-axis is perpendicular to the interface y-axis;
   an interface revolute joint, where the interface revolute joint is a single degree of freedom joint allowing rotation about a single joint rotation axis, where the single joint rotation axis is perpendicular to the interface y-axis;
   a user end-effector;
   a first serial linkage, where a first end of the first serial linkage is anchored by the 2 DOF interface universal joint, and where a second end of the first serial linkage is pinned at the interface revolute joint, and where a first linkage length is equal to a displacement from the first end of the first serial linkage to the second end of the first serial linkage;

a second serial linkage, where a first end of the second serial linkage is pinned at the interface revolute joint, and where a second end of the second serial linkage is attached to the user end-effector, such that the first serial linkage and the second serial linkage comprise an interface planar linkage having motion constrained to an interface linkage motion plane, where the interface y-axis resides in or is parallel to the interface linkage motion plane, and where a second linkage length is equal to a displacement from the first end of the second serial linkage to the user end-effector;

a palm anchoring surface fixably attached to the palm anchoring section, where the palm anchoring surface is fixably attached to the palm anchoring section such that the interface planar linkage comprised of the first serial linkage and the second serial linkage can rotate about the interface x-axis to a position where the end-effector at the second end of the second serial linkage is within at least 200 millimeters of the palm anchoring surface;

a first joint angle sensor for determining a first angle, where the first angle is an angle between an interface y-z plane and the interface linkage motion plane, where the interface y-z plane is defined by the interface y-axis and an interface z-axis, where the interface z-axis is perpendicular to the interface y-axis and perpendicular to the interface x-axis, and where the first joint angle sensor is in data communication with the digital controller;

a second joint angle sensor for determining a second angle, where the second angle is an angle between the first serial linkage and an interface x-z plane, where the interface x-z plane is defined by the interface x-axis and the interface z-axis, and where the second joint angle sensor is in data communication with the digital controller; and a third joint angle sensor for determining a third angle, where the third angle is a joint angle between the first serial linkage and the second serial linkage in the interface linkage motion plane, and where the third joint angle sensor is in data communication with the digital controller.

3. The user interface of claim 2 where the digital controller is further programmed for:

receiving the first angle, the second angle, and the third angle from the fingertip locator;

evaluating a location of the user end-effector relative to the fixed reference point using forward kinematics and at least the first angle, the second angle, the third angle, the first linkage length, and the second linkage length; and assigning the specific fingertip location to the location of the user end-effector, thereby reading the specific fingertip location relative to the fixed reference point from the fingertip locator.

4. The user finger interface of claim 1 further comprised of:

a robotic hand, where the robotic hand is comprised of a robotic finger, where the robotic finger is comprised of, a robotic MCP joint, where the robotic MCP joint has at least a first robotic rotational degree of freedom and a second robotic rotational degree of freedom, where the first robotic rotational degree of freedom is a rotation about a robotic x-axis and where the second robotic rotational degree of freedom is a rotation about a robotic y-axis, where the robotic x-axis is perpendicular to the robotic y-axis, a robotic PIP joint, where the robotic PIP joint has at least one degree of freedom, where the one degree of freedom allows rotation about a single robotic rotation axis, where the single robotic rotation axis perpendicular to the robotic y-axis, a robotic proximal phalange, where a first end of the robotic proximal phalange is anchored by the robotic MCP joint, and where a second end of the robotic proximal phalange is pinned at the robotic PIP joint, and where a robotic proximal phalange length is equal to a displacement from the first end of the robotic proximal phalange to the second end of the robotic proximal phalange and, a robotic intermediate-distal phalange, where a first end of the robotic intermediate-distal phalange is pinned at the robotic PIP joint, and where a second end of the intermediate-distal phalange is attached to a robotic end-effector, and where a robotic intermediate-distal phalange length is equal to a displacement from the first end of the robotic intermediate-distal phalange to the second end of the robotic intermediate-distal phalange; and a robotic hand controller in data communication with the robotic hand and in data communication with the data port of the digital controller.

5. The user interface of claim 4 where a robotic length ratio is equal to the robotic proximal phalange length divided by the robotic intermediate-distal phalange length, and where the robotic length ratio is within 10% of a user length ratio, such that the robotic length ratio divided by the user length ratio is greater than or equal to 0.9 and less than or equal to 1.1.

6. The user interface of claim 5 where the robotic proximal phalange and the robotic intermediate-distal phalange comprise a robotic planar linkage having motion constrained to a robotic linkage motion plane, where the robotic y-axis resides in or is parallel to the robotic linkage motion plane, and where the digital controller is further programmed to communicate the first MCP angle, the second MCP angle, and the PIP angle to the robotic hand controller, and where the robotic finger is further comprised of:

a first joint positioning means, where the first joint positioning means is connected to the robotic proximal phlange, and where the first joint positioning means is in data communication with the robotic hand controller, and a second joint positioning means where the second joint positioning means is connected to the robotic proximal phlange and connected to the robotic intermediate-distal phalange, and where the second joint positioning means is in data communication with the robotic hand controller.

7. A method of operating the user interface of claim 1 comprising:

placing a user's palm in contact with the palm anchoring section, and placing a fingertip of a user's finger in contact with the fingertip locator;

positioning the fingertip of the user's finger at a calibration point while maintaining the user's finger is a substantially straight position and while maintaining the fingertip of the user's finger in contact with the fingertip locator, and allowing the fingertip locator to communicate data to the digital controller, where the data defines a location of a single calibration point relative to the fixed reference point;

permitting the digital controller to evaluate the data communicated from the fingertip locator to the digital controller and define the location of the single calibration point relative to the fixed reference point and generate a calibration point location relative to the fixed reference point, and allowing the digital controller to record the calibration point location;

repeating the positioning step and the permitting step until the plurality of calibration point locations is generated; and allowing the digital controller to define the center of the calibration sphere using the plurality of calibration point locations and determine the calibration sphere radius, and allowing the digital controller to establish the user MCP joint location at the center of the calibration sphere, thereby determining the user MCP joint location relative to the fixed reference point, and allowing the digital controller to determine the user finger length based on the calibration sphere radius and divide the user finger length into the first length and the second length based on the user finger length, and establish the user proximal phalange length equal to the first length and establish the user intermediate-distal phalange length equal to the second length, and thereby conduct the calibration procedure and determine the user MCP joint location relative to the fixed reference a point, the user proximal phalange length, and the user intermediate-distal phalange length;

re-positioning the fingertip locator using the user's finger and allowing the digital controller to read the specific fingertip location from the fingertip locator;

permitting the digital controller to define the user planar linkage comprised of the first link, the 2 DOF universal joint, the first rotational degree of freedom, the second rotational degree of freedom, the user x-axis, the user y-axis, the revolute joint, the single rotation axis, the second link, and the user linkage motion plane, and allowing the digital controller to determine the first MCP angle, the second MCP angle, and the PIP angle for the specific fingertip location using the inverse kinematics and the user planar linkage, the user y-z plane, and the user z-axis; and allowing the digital controller to communicate the first MCP angle, the second MCP angle, and the PIP angle through the data port.

8. The user interface of claim 2 further comprised of:

a supination/pronation joint attached to the palm anchoring section, where the supination/pronation joint has a rotational degree of freedom about a supination/pronation axis;

an extension/flexion joint attached to the supination/pronation joint, where the extension/flexion joint has a rotational degree of freedom about an extension/flexion axis;

a radial/ulnar joint attached to the extension/flexion joint, where the radial/ulnar joint has a rotational degree of freedom about a radial/ulnar axis, and where the radial/ulnar axis is parallel to or resides within the user y-z plane, the extension/flexion axis is perpendicular to the radial ulnar axis, and the supination/pronation axis is perpendicular to the extension/flexion axis and the radial ulnar axis.

9. The user interface of claim 1 where the digital controller is programmed to establish the user finger length equal to a value within 95% to 105% of the calibration sphere radius, such that the user finger length divided by the calibration sphere radius is greater than or equal to 0.95 and less than or equal to 1.05.

10. The user interface of claim 9 where the digital controller is programmed to divide the user finger length into the first length and the second length such that the first length plus the second length is greater than or equal to 0.95 times the user finger length and less than or equal to 1.05 times the user finger length.

11. The user interface of claim 10 where the digital controller is programmed to divide the user finger length into the first length and the second length such that the first length divided by the second length is within 10% of a user length ratio, such that the first length divided by the second length is greater than or equal to 0.90 times the user length ratio and less than or equal to 1.10 times the user length ratio.

12. The user interface of claim 11 where the quantity of calibration point locations in the plurality of calibration point locations is equal to four, and where the digital controller is programmed to establish the calibration sphere as a sphere having a surface that intersects each of the four calibration point locations and define the center of the calibration sphere as the center of the sphere having the surface that intersects each of the four calibration point location.

13. The user interface of claim 10 where the user interface is comprised of a plurality of fingertip locators, where each fingertip locator in the plurality of fingertip locators is in data communication with the digital controller, and where the digital controller is programmed for receiving an individual plurality of calibration point locations from the each fingertip locator and conducting the calibration procedure by utilizing the individual plurality of calibration point locations as the plurality of calibration point locations, and thereby determining a user MCP joint location for the each fingertip locator, a user proximal phalange length for the each fingertip locator, and a user intermediate-distal phalange length for the each fingertip locator.

14. The user interface of claim 13 where the user interface is further comprised of a robotic hand, where the robotic hand is comprised of a plurality of robotic fingers, and where a quantity of robotic fingers in the plurality of robotic fingers is at least equal to a quantity of fingertip locators in the plurality of fingertip locators, and where each robotic finger in the plurality of robotic fingers is in data communication with a robotic hand controller, where the robotic hand controller is in data communication with the digital controller.

15. A user interface for determining a first MCP angle, a second MCP angle, and a PIP angle, where MCP denotes metacarpophalangeal and where PIP denotes proximal interphalangeal, comprising:

a fingertip locator, where the fingertip locator defines a location relative to a fixed reference point;

a palm anchoring section;

digital controller in data communication with the fingertip locator, where the digital controller is comprised of a data port, and where the digital controller is programmed for, conducting a calibration procedure and determining a user MCP joint location relative to the fixed reference point, a user proximal phalange length, and a user intermediate-distal phalange length by, receiving a plurality of calibration point locations from the fingertip locator, where each calibration point location in the plurality of calibration point locations has a unique location relative to the fixed reference point, and where a quantity of calibration point locations in the plurality of calibration point locations is equal to at least four, defining a center of a calibration sphere using the plurality of calibration point locations, and determining a calibration sphere radius of the calibration sphere, establishing the user MCP joint location at the center of the calibration sphere, thereby determining the user MCP joint location relative to the fixed reference point and, determining a user finger length based on the calibration sphere radius, and dividing the user finger length into a first length and a second length based on the user finger length, and establishing the user proximal phalange length equal to the first length and establishing the user intermediate-distal phalange length equal to the second length, thereby determining the user proximal phalange length and the user intermediate-distal phalange length, and thereby conducting the calibration procedure and, determining the first MCP angle, the second MCP angle, and the PIP angle by, reading a specific fingertip location relative to the fixed reference point from the fingertip locator;

defining a user planar linkage comprised of, a first link, where a displacement from a first end of the first link to a second end of the first link is equal to the user proximal phalange length, and where the first end of the first link is located at the user MCP joint location and anchored by a 2 DOF universal joint, where the 2 DOF universal joint has a first rotational degree of freedom and a second rotational degree of freedom, where the first rotational degree of freedom is a rotation about a user x-axis and where the second rotational degree of freedom is a rotation about a user y-axis, where the user x-axis is perpendicular to the user y-axis, and where the second end of the first link is pinned at a revolute joint, where the revolute joint is a single degree of freedom joint allowing rotation about a single rotation axis, where the single rotation axis is perpendicular to the user y-axis and, a second link, where a displacement from a first end of the second link to a second end of the second link is equal to the user intermediate-distal phalange length, and where the second end of the second link is located at the specific fingertip location, and where the first end of the second link is pinned at the revolute joint, such that the user planar linkage has motion constrained to the user linkage motion plane, where the user y-axis resides in or is parallel to the user linkage motion plane and, defining the first MCP angle, the second MCP angle, and the PIP angle for the specific fingertip location using inverse kinematics and the user planar linkage, where the first MCP angle is an angle between a user y-z plane and the user linkage motion plane, where the user y-z plane is defined by the user y-axis and a user z-axis, where the user z-axis is perpendicular to the user x-axis and perpendicular to the user y-axis, and where the second MCP angle is an angle between the first link and a user x-z plane, where the user x-z plane is defined by the user x-axis and the user z-axis, and where the PIP angle is a joint angle between the first link and the second link in the user linkage motion plane, thereby determining the first MCP angle, the second MCP angle, and the PIP angle and, communicating the first MCP angle, the second MCP angle, and the PIP angle through the data port;

a robotic hand, where the robotic hand is comprised of a robotic finger, where the robotic finger is comprised of, a robotic MCP joint, where the robotic MCP joint has at least a first robotic rotational degree of freedom and a second robotic rotational degree of freedom, where the first robotic rotational degree of freedom is a rotation about a robotic x-axis and where the second robotic rotational degree of freedom is a rotation about a robotic y-axis, where the robotic x-axis is perpendicular to the robotic y-axis, a robotic PIP joint, where the robotic PIP joint has at least one degree of freedom, where the one degree of freedom allows rotation about a single robotic rotation axis, where the single robotic rotation axis perpendicular to the robotic y-axis, a robotic proximal phalange, where a first end of the robotic proximal phalange is anchored by the robotic MCP joint, and where a second end of the robotic proximal phalange is pinned at the robotic PIP joint, and where a robotic proximal phalange length is equal to a displacement from the first end of the robotic proximal phalange to the second end of the robotic proximal phalange and, a robotic intermediate-distal phalange, where a first end of the robotic intermediate-distal phalange is pinned at the robotic PIP joint, and where a second end of the intermediate-distal phalange is attached to a robotic end-effector, and where a robotic intermediate-distal phalange length is equal to a displacement from the first end of the robotic intermediate-distal phalange to the second end of the robotic intermediate-distal phalange, and where a robotic length ratio is equal to the robotic proximal phalange length divided by the robotic intermediate-distal phalange length, where the robotic length ratio is within 10% of a user length ratio, such that the robotic length ratio divided by the user length ratio is greater than or equal to 0.9 and less than or equal to 1.1; and a robotic hand controller in data communication with the robotic hand and in data communication with the data port of the digital controller.

16. The user finger interface of claim 15 where the fingertip locator is comprised of;

a 2 DOF interface universal joint fixably attached to the palm anchoring section, where the 2 DOF interface universal joint has a first joint rotational degree of freedom and a second joint rotational degree of freedom, where the first joint rotational degree of freedom is a rotation about an interface x-axis and where the second joint rotational degree of freedom is a rotation about an interface y-axis, where the interface x-axis is perpendicular to the interface y-axis;

an interface revolute joint, where the interface revolute joint is a single degree of freedom joint allowing rotation about a single joint rotation axis, where the single joint rotation axis is perpendicular to the interface y-axis;

a user end-effector;

a first serial linkage, where a first end of the first serial linkage is anchored by the 2 DOF interface universal joint, and where a second end of the first serial linkage is pinned at the interface revolute joint, and where a first linkage length is equal to a displacement from the first end of the first serial linkage to the second end of the first serial linkage;

a second serial linkage, where a first end of the second serial linkage is pinned at the interface revolute joint, and where a second end of the second serial linkage is attached to the user end-effector, such that the first serial linkage and the second serial linkage comprise an interface planar linkage having motion constrained to an interface linkage motion plane, where the interface y-axis resides in or is parallel to the interface linkage motion plane, and where a second linkage length is equal to a displacement from the first end of the second serial linkage to the user end-effector;

a palm anchoring surface fixably attached to the palm anchoring section, where the palm anchoring surface is fixably attached to the palm anchoring section such that the interface planar linkage comprised of the first serial linkage and the second serial linkage can rotate about the interface x-axis to a position where the end-effector at the second end of the second serial linkage is within at least 200 millimeters of the palm anchoring surface;

a first joint angle sensor for determining a first angle, where the first angle is an angle between an interface y-z plane and the interface linkage motion plane, where the interface y-z plane is defined by the interface y-axis and an interface z-axis, where the interface z-axis is perpendicular to the interface y-axis and perpendicular to the interface x-axis, and where the first joint angle sensor is in data communication with the digital controller;

a second joint angle sensor for determining a second angle, where the second angle is an angle between the first serial linkage and an interface x-z plane, where the interface x-z plane is defined by the interface x-axis and the interface z-axis, and where the second joint angle sensor is in data communication with the digital controller; and a third joint angle sensor for determining a third angle, where the third angle is a joint angle between the first serial linkage and the second serial linkage in the interface linkage motion plane, and where the third joint angle sensor is in data communication with the digital controller.

17. The user interface of claim 16 where the digital controller is programmed to establish the user finger length equal to a value within 95% to 105% of the calibration sphere radius, such that the user finger length divided by the calibration sphere radius is greater than or equal to 0.95 and less than or equal to 1.05.

18. The user interface of claim 17 where the digital controller is programmed to divide the user finger length into the first length and the second length such that the first length plus the second length is greater than or equal to 0.95 times the user finger length and less than or equal to 1.05 times the user finger length.

19. The user interface of claim 18 where the digital controller is programmed to divide the user finger length into the first length and the second length such that the first length divided by the second length is within 10% of a user length ratio, such the first length divided by the second length is greater than or equal to 0.90 times the user length ratio and less than or equal to 1.10 times the user length ratio.

* * * * *